United States Patent [19]

Lacy

[11] Patent Number: 5,355,870
[45] Date of Patent: Oct. 18, 1994

[54] LARYNGOSCOPE HAVING REMOVABLE BLADE ASSEMBLY CONTAINING LAMP AND LIGHT CONDUCTOR

[76] Inventor: William Lacy, 26 Steers Ave., Northport, N.Y. 11768

[21] Appl. No.: 920,677

[22] Filed: Jul. 28, 1992

[51] Int. Cl.$^5$ ............................................. A61B 1/06
[52] U.S. Cl. ........................................ 128/11; 128/10
[58] Field of Search ...................... 128/10, 11, 15, 16, 128/17, 18, 6

[56] References Cited

U.S. PATENT DOCUMENTS

| | | | |
|---|---|---|---|
| 2,289,226 | 7/1942 | Von Foregger | 128/11 |
| 2,354,471 | 7/1944 | Macintosh | 128/10 |
| 2,433,705 | 12/1947 | Palmeter | 128/10 |
| 4,273,112 | 6/1981 | Heine et al. | 128/11 |
| 4,556,052 | 12/1985 | Muller | 128/11 |
| 4,557,256 | 12/1985 | Bauman | 128/11 |
| 4,565,187 | 1/1986 | Soloway | 128/11 |
| 4,570,614 | 2/1986 | Bauman | 128/11 |
| 4,583,528 | 4/1986 | Bauman | 128/11 |
| 4,901,708 | 2/1990 | Lee | 128/6 X |
| 4,958,624 | 9/1990 | Stone et al. | 128/11 |

Primary Examiner—Richard J. Apley
Assistant Examiner—Beverly A. Meindl
Attorney, Agent, or Firm—Edward H. Loveman

[57] ABSTRACT

This laryngoscope has a cylindrical metal casing serving as a handle. An insulated, plastic blade is rotatably mounted near one end thereof on the casing between angularly spaced operating and nonoperating positions. A blade projects from the blade assembly to depress a patient's tongue. Batteries in the casing apply positive electric polarity to an electrode on the casing and negative electric polarity to the casing. A lensed end lamp having a bulb, base and end terminal is mounted on the blade assembly with the terminal in contact with a leaf spring which in turn contacts the electrode when the assembly is rotated to an operating position. A flange on the casing contacts the lamp base to complete a power supply circuit when the blade assembly is rotated to the operating position for lighting the lamp bulb. A light conductive rod extends from the lamp bulb to project light into the patient's larynix while the blade depresses the patient's tongue. A hook on the blade assembly enables easy mounting of the blade assembly on the casing and easy removal therefrom.

10 Claims, 2 Drawing Sheets

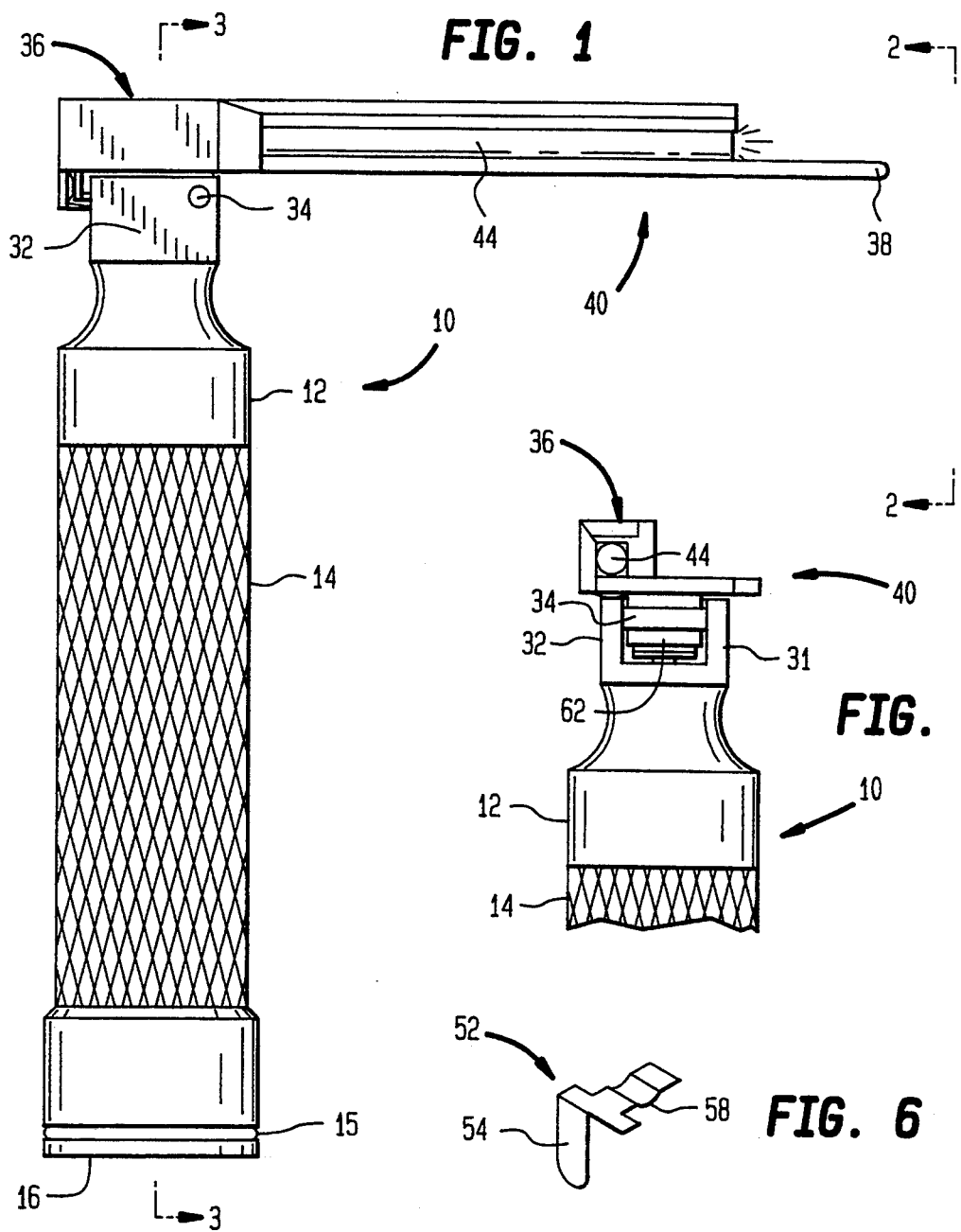

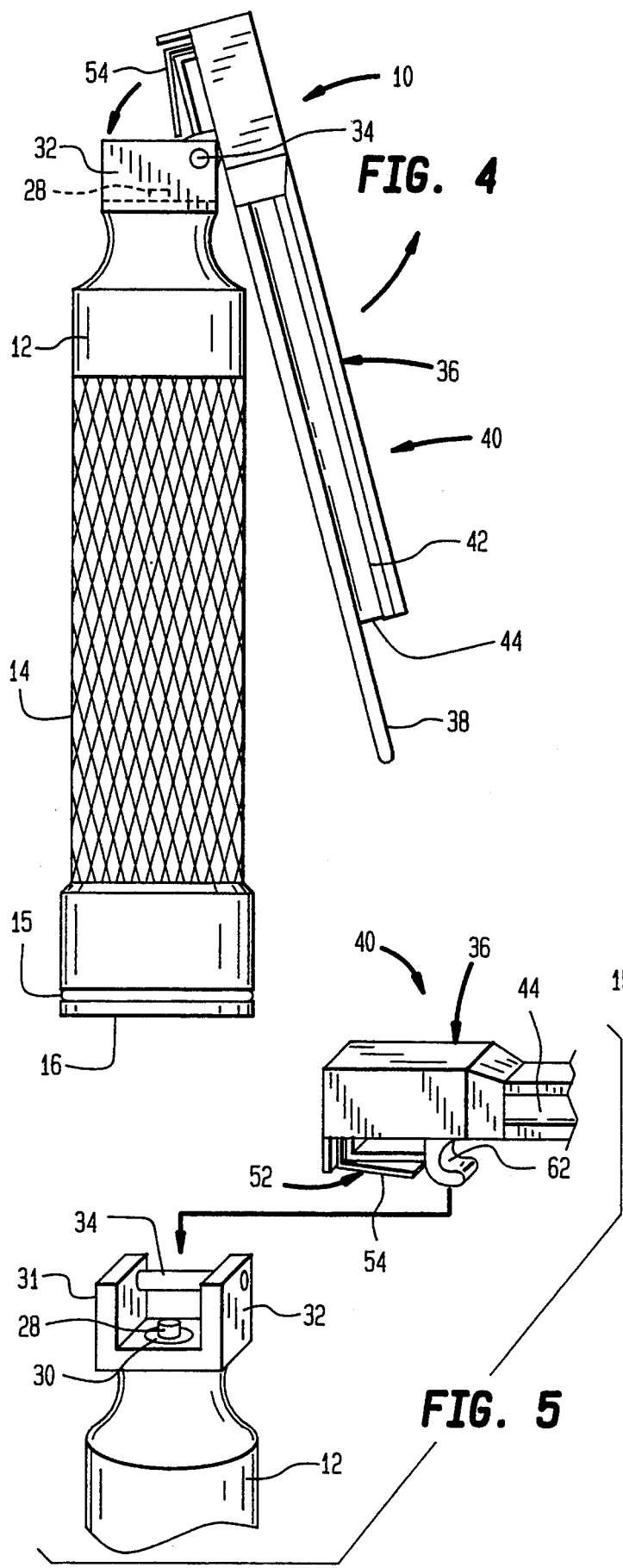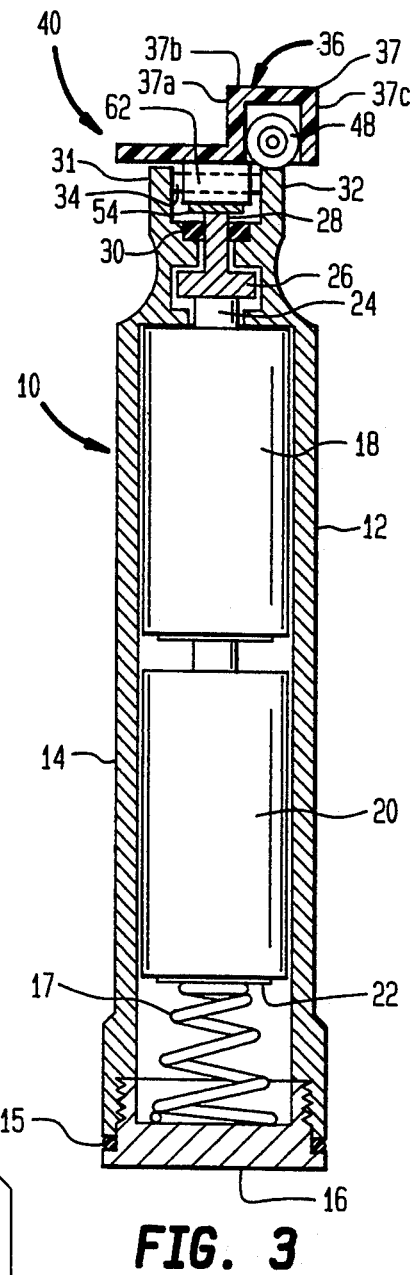

LARYNGOSCOPE HAVING REMOVABLE BLADE ASSEMBLY CONTAINING LAMP AND LIGHT CONDUCTOR

BACKGROUND OF THE INVENTION

1. Field of the Invention

This invention relates to improvements in laryngoscopes used for examining the larynx of a patient; and more particularly concerns a laryngoscope having a handle for accommadating a rotatable, removable blade assembly containing a light conductor and lamp powered by batteries in the handle.

2. Description of the Prior Art

It is known to provide a laryngoscope with a handle carrying a plurality of batteries for energizing a lamp. The handle accommadates a removable blade which serves as a tongue depressor. The blade may carry a light conductor to convey light from the lamp to the larynx which is to be visualized. None of the prior art laryngoscopes have an inexpensive disposable blade carrying both lamp and light conductor rod, with contact means for energizing the lamp only when the blade is in operating position.

SUMMARY OF THE INVENTION

The present invention is directed at providing an improved laryngoscope which avoids the deficiencies of prior known laryngoscopes. According to the invention, the laryngoscope has a metal cylindrical casing containing a plurality of batteries. The casing serves as a handle for the laryngoscope blade. At one end the batteries are in contact with a coil spring through which negative polarity is conveyed to the casing. At the other end the batteries are in contact with a central electrode which is maintained continuously at positive polarity. The casing has upstanding flanges with a cross pin rotatably carrying a removable blade assembly. The blade assembly has an inexpensive, plastic body into which is inserted a transparent light conducting rod in direct contact with the bulb of a lensed end lamp. The lamp has an electrically conductive base and a entral terminal insulated from the lamp base. The blade assembly can be rotated between an operating and a nonoperating position on the casing or handle. In the operating position, a conductive leaf spring member is in direct contact with the central electrode having positive polarity. The leaf spring member is also in contact with the central terminal of the lamp, to apply a positive polarity to the lamp. At the same time one of the flanges carrying the cross pin on which the blade assembly is mounted is in direct contact with a side of the metal lamp base so that negative electrical polarity is applied to the lamp base. This causes the lamp to light and to project its light through the light conductor rod carried by the blade body, forwardly to illuminate the larynx of a patient while the blade is used to depress the tongue. When the blade assembly is rotated on the battery casing to a nonoperating position, the flange on the casing separates from the lamp base and at the same time the leaf spring separates from the terminal electrode of the batteries. This opens the power supply circuit for the lamp and its light is extinguished. The blade assembly can easily be removed after use and discarded, and another blade assembly can be quickly mounted in its place on the battery casing.

It is therefore a principal object of the present invention to provide a laryngoscope having an inexpensive and disposeable laryngoscope blade.

It is a further object of the present invention to provide a laryngoscope having an inexpensive and disposeable laryngoscope blade which has a self contained light source and fiber optic tube.

It is another object of the present invention to provide a laryngoscope having an inexpensive and disposeable laryngascope blade which utilizes a conventional lensed bulb as a source of light.

These and other object and many of the attendant advantages of this invention will be readily appreciated as the same becomes better understood by reference to the following detailed description when considered in connection with the accompanying drawings in which:

BRIEF DESCRIPTION OF THE DRAWINGS

FIG. 1 is a side elevational view of the laryngoscope embodying the invention, with blade assembly shown in operating position, the power supply circuit to the lamp being closed;

FIG. 2 is a fragmentary front elevational view taken along line 2—2 of FIG. 1;

FIG. 3 is an axial sectional view taken along line 3—3 of FIG. 1;

FIG. 4 is a side elevational view similar to FIG. 1, with blade assembly shown rotated to nonoperating position;

FIG. 5 is a fragmentary exploded perspective view of an end part of the battery casing or handle and an end portion of the blade assembly, which engages rotatably on the end part of the battery casing;

FIG. 6 is a perspective view of the leaf spring per se which serves as a contact member to the central electrode of the batteries and to the terminal of the lamp;

FIG. 7 is a perspective view of the blade assembly per se shown in an inverted position;

FIG. 8 is an enlarged fragmentary sectional view taken along line 8—8 of FIG. 8, showing associated parts of the blade assembly.

DESCRIPTION OF THE PREFERRED EMBODIMENTS

Referring now to the drawings wherein like reference characters designate like or corresponding parts throughout, there is illustrated in FIGS. 1 to 4, a laryngoscope 10 having a hollow cylindrical metal casing 12. The casing has scoring or knurling 14 on the outside to provide a slip-proof handgrip to the casing 12 which serves as a handle for the laryngoscope. A screw cap 16 and a gasket 15 are removably engaged in the bottom of the casing 12. The cap 16 carries a coil spring 17 which extends axially upwardly in the interior of the casing 16. Inside the casing 12 are a pair of dry-cell batteries 18, 20. The coil spring 17 bears upwardly against the bottom of a metal case 22 of the battery 20 thereby applying a negative electrical polarity to the casing 12. A positive terminal 24 of the upper battery 18 bears against a metal plug 26 which terminates in a central upwardly projecting terminal electrode 28 at the top of the casing 12. Positive electrical polarity is applied to the electrode 28 from the terminal 24 of the battery 18. An annular insulator 30 set in the top of the casing 12 surrounds the electrode 28 and holds it in place. Extending upwardly from the top of the casing 12 are two integral metal flanges 31, 32. The flanges 31,32 are parallel and carry a horizontal cross pin 34; see FIGS. 2 and 5.

A blade assembly 40 generally designated as reference numeral 40 is rotatably and removably mounted on the pin 34. The blade assembly 40 has an opaque plastic body 36 terminating at its forward end in a blade 38 which serves as a tongue depressor in a patient. The body 36 has a longitudinal, lateral channel 42 in which is set a transparent plastic light conductor rod 44. Rearwardly of the rod 44 is a lamp assembly 46 encompassed in a housing 37 integral with the blade assembly 40 having walls 37a, 37b and 37c, as illustrated in FIG. 3; see FIGS. 3, 7 and 8. The lamp assembly 46 is disposed axially parallel to the rod 4 and is comprised of a transparent lensed light emitting lamp bulb 47, a metallic base 48 and a central, metal terminal 50. A leaf spring 52 as best shown in FIG. 6 has a generally L-shaped configuration. A flexible tongue 54, from the leaf spring 52 extends laterally out of a channel 56 in the plastic body 36. The rear end portion 58 of the spring 52 extends through the channel 56 in the body 36 and makes firm contact with the terminal 50 of the bulb 47; see FIGS. 3, 7 and 8. The body 36 is formed with an integral hook 62 which can easily be engaged on the cross pin 34 and can easily be removed therefrom.

When the blade assembly 40 is in the upright position, as shown in FIGS. 1 and 2, the conductive tongue 54 contacts the exposed top of the central electrode 28. This applies a positive electrical polarity to the bulb 47 via the bulb terminal 50. At the same time the flange 32 is pressed into firm direct contact with a side 49 of the base 48; see FIG. 3. This applies a negative electrical polarity to the bulb 47 and the bulb lights, as soon as and as long as the blade assembly 40 is held in the raised position shown in FIG. 1. When the blade assembly 40 is lowered to the position shown in FIGS. 4, the tongue 54 separates from the top of the central electrode 28, and at the same time the side 48 of the bulb 47 separates from the flange 32. Thus the positive and negative circuit paths from the batteries 18, 20 are simultaneously broken. The blade assembly 40 thus serves as a single throw, double pole switch to close and open the power supply circuit for the lamp assembly 46.

After a single use, the entire blade assembly 40 can be removed by lifting if off of the cross pin 34. The plastic body 36, the rod 44, the lamp assembly 46 and the leaf spring 52 can all be discarded at the same time, so that the cross pin 34 is ready to receive another replacement blade assembly 40 for reuse of the laryngoscope 10. The double pole switch arrangement of the spring 52 and the side 48 of the bulb 47 insures an uninterrupted power supply to the lamp assembly 46 when the blade assembly 40 is in the operating position of FIG. 1 and insures that the lamp assembly 46 is extinguished when the blade assembly 40 is in the nonoperating position of FIG. 4. This conserves the batteries against accidental turn-on and unnecessary power consumption.

The lensed bulb 47 may be a conventional flashlight bulb such as Penlite 222. If desired a parabolic reflector 59 as illustrated in phantom in FIG. 8, may be inserted over the bulb 47 to increase the light intensity of the light transmitted to the conductor rod 44.

It should be understood that the foregoing relates to only a limited number of preferred embodiments of the invention which have been by way of example only, and that is intended to cover all changes and modifications of the examples of the invention herein chosen for the purposes of the disclosure, which do not constitute departures from the spirit and scope of the invention.

What is claimed is:

1. A laryngoscope, comprising:
   an electrically conductive casing closed at one end and having an electrode at said other end of said casing;
   battery means in said casing arranged to apply a positive electric polarity to said electrode and a negative electric polarity to said casing;
   an elongated insulated blade assembly, removably mounted near one end thereof, on said other end of said casing and rotatable thereon, between operating and nonoperating positions spaced angularly apart;
   a lensed end lamp enclosed in a housing integral with said blade assembly at said one end thereof, said lamp having a bulb, a base and an end terminal;
   first circuit means carried by said blade assembly and arranged to contact said end terminal of said lamp to apply said positive electric polarity thereto from said electrode when said blade assembly is in said operating position; and
   second circuit means carried by said casing and contacting said base of said lamp, for lighting said lamp only when said blade assembly is in said operating position, and for extinguishing said lamp when said blade assembly is rotated to said nonoperating position.

2. A laryngoscope as claimed in claim 1, wherein said blade assembly has an axial projecting blade at another end thereof, to depress the tongue of a patient, when said lamp illuminates the larynix of a patient during examination thereof.

3. A laryngoscope as claimed in claim 2, further comprising a light conducting rod mounted on said blade assembly in contact with said bulb of said lamp at one end of said rod to conduct light therefrom, said rod having its other end disposed on said blade for conducting light from said lamp through said rod to the larynix of said patient when said blade depresses said tongue of said patient.

4. A laryngoscope as claimed in claim 3, wherein said casing has a pair of parallel flanges at said one enid of said casing, and a cross pin connecting said flanges to serves as a support for said blade assembly in rotating thereon between said operating and said nonoperating positions.

5. A laryngoscope as claimed in claim 4, wherein said one end of said blade assembly is formed with a hook detachably engaged with said cross pin for rotating thereon, and for removing said blade assembly therefrom.

6. A laryngoscope as claimed in claim 4, wherein said lamp base is laterally exposed on said blade assembly for contacting one of said flanges when said blade assembly is rotated to said operating position, to apply said negative electrical polarity from said casing to said lamp.

7. A laryngoscope as claimed in claim 6, wherein said first circuit means comprises a metallic electrical conductor having one portion in contact with said end terminal of said lamp and a free portion engageable with said electrode when said blade assembly is in said operating position.

8. A laryngoscope as claimed in claim 7, wherein said one flange constitutes said second circuit means for applying said negative polarity from said casing to said lamp.

9. A laryngoscope as claimed in claim 8, wherein said metallic electric conductor and said one flange cooperate to constitute said single throw, double throw switch means for lighting said lamp when said blade assembly is in said operating position.

10. A laryngoscope as claimed in claim 3 further including a parabolic reflector surrounding said lamp for increasing the intensity oof light transmitted to said to said light conducting rod.

* * * * *